US007888476B2

(12) United States Patent
Martel et al.

(10) Patent No.: US 7,888,476 B2
(45) Date of Patent: Feb. 15, 2011

(54) PROCESS FOR THE PREPARATION OF A VON WILLEBRAND (FVW) FACTOR CONCENTRATE BY CHROMATOGRAPHY AND A FVW CONCENTRATE THUS OBTAINABLE

(75) Inventors: Serge Martel, La Madeleine (FR); Sami Chtourou, Elancourt (FR); Michel Poulle, Wavrin (FR)

(73) Assignee: Laboratoire Francais du Fractionnement Et des, Les Ulis (FR)

( * ) Notice: Subject to any disclaimer, the term of this patent is extended or adjusted under 35 U.S.C. 154(b) by 1010 days.

(21) Appl. No.: 11/203,655

(22) Filed: Aug. 12, 2005

(65) Prior Publication Data

US 2006/0036081 A1 Feb. 16, 2006

(30) Foreign Application Priority Data

Aug. 16, 2004 (FR) .................................. 04 08897

(51) Int. Cl.
 *C07K 14/775* (2006.01)
(52) U.S. Cl. .................. 530/383; 530/350; 530/300; 435/7.1; 514/12
(58) Field of Classification Search .................. None
 See application file for complete search history.

(56) References Cited

U.S. PATENT DOCUMENTS

| 4,342,748 | A | * | 8/1982 | Pappenheimer et al. ..... 424/545 |
| 5,252,709 | A | | 10/1993 | Burnouf et al. |
| 5,408,039 | A | * | 4/1995 | Burnouf-Radosevich et al. . 530/383 |
| 5,679,776 | A | | 10/1997 | Burnouf-Radosevich et al. |
| 5,854,403 | A | | 12/1998 | Fischer et al. |
| 6,239,261 | B1 | | 5/2001 | Heimburger et al. |
| 6,465,624 | B1 | * | 10/2002 | Fischer et al. ............... 530/412 |
| 6,518,482 | B2 | | 2/2003 | Lubon et al. |
| 6,531,577 | B1 | | 3/2003 | Kaersgaard et al. |
| 6,579,723 | B1 | | 6/2003 | Mitterer et al. |

FOREIGN PATENT DOCUMENTS

| EP | 0359593 A1 | 3/1990 |
| EP | 0383234 A2 | 8/1990 |
| EP | 0416983 A1 | 3/1991 |
| EP | 0503991 A1 | 9/1992 |
| EP | 0934748 A2 | 8/1999 |
| FR | 0308403 | 9/2003 |

OTHER PUBLICATIONS

Makris et al. "Venous thrombosis following the use of intermediate purity FVIII concentrate to treat patients with von Willebrand's disease." Thromb Haemost Sep. 2002; 88(3):378-9.
Mannucci, "Venous thromboembolism in von Willebrand disease." Thromb Haemost. Sep. 2002; 88(3):378-9.
Cohn et al. "Preparation and Properties of Serum and Plasma Proteins. IV. A System for the Separation Into Fractions of the Protein and Lipoprotein Components of Biological Tissues and Fluids." J Am Chem Soc. Mar. 1946. vol. 8 pp. 459-75.
Kistler et al. "Large scale production of human plasma fractions. Eight years experience with the alcohol fractionation procedure of Nitschmann, Kistler and Lergier." Vox Sang. Jul.-Aug. 1962; 7:414-24.
Burnouf. "Chromatography in plasma fractionation: benefits and future trends." Journal of Chromatography B: Biomedical Applications. Feb. 3, 1995;664(1):3-15.

* cited by examiner

*Primary Examiner*—Hope A Robinson
(74) *Attorney, Agent, or Firm*—Birch, Stewart, Kolasch & Birch, LLP

(57) ABSTRACT

This invention relates to a process for the preparation of a very high purity von Willebrand factor concentrate from a biological fraction containing von Willebrand factor, including a separation by anion exchange chromatography using a vinyl polymer support of weak base type, the separation comprising the steps of loading of the chromatographic support with the fraction containing von Willebrand factor, previously equilibrated with a suitable buffer, with a predetermined flowrate allowing the retention of the von Willebrand factor, washing of the support with an acidic buffer with a flowrate higher than the flowrate of the step a) until the not-retained proteins and the contaminants are removed, flushing and equilibrating of the chromatographic support with the buffer and using the flowrate of the step a), and elution of the von Willebrand factor by increasing of the ionic strength of the step c). The invention also relates to a von Willebrand factor concentrate for therapeutic use likely to be obtained by implementing the process wherein the rate of Factor VIII:C/FvW:RCo is less than 0.06%.

13 Claims, No Drawings

PROCESS FOR THE PREPARATION OF A VON WILLEBRAND (FVW) FACTOR CONCENTRATE BY CHROMATOGRAPHY AND A FVW CONCENTRATE THUS OBTAINABLE

This Nonprovisional application claims priority under 35 U.S.C. §119 of French priority document 0408897, filed on Aug. 16, 2004, the entire contents of which are hereby incorporated by reference.

FIELD OF THE INVENTION

This invention relates to a process for the preparation of a von Willebrand factor (FvW) concentrate by chromatography and to a thus obtainable concentrate of FvW.

BACKGROUND OF RELATED ART

The von Willebrand factor is a multimetric blood protein with molecular weights within of about 200 kDa and of about 20 000 kDa, and even more. This protein, that is synthetised by blood platelets and endothelial cells, plays a key role in the struggle against bleeding insofar as the FvW acts as a gelifying plug which spreads over a vascular breach providing for the adhesion of platelets in order to carry out the first phase of the hemostasis, namely the formation of a "platelet-thrombus" (thrombus). The coagulation phenomena, intended to consolidate the arrest of the bleeding by forming an insoluble fibrin clot, will take place around this thrombus. In the blood circulation, the FvW ensures also the stabilization and the transport of Factor VIII with which it is associated in complexes of various sizes, said Factor VIII being thus protected against a rapid degradation by proteolysis because of the sensitivity of the isolated Factor VIII to proteases.

A congenital deficiency of FvW or genetic mutations, that modify the properties of FvW, causes the Willebrand disease which is indicated by troubles of primary hemostasis and of blood clotting.

The availability of very high purity human plasma derivatives enriched by FvW, suitable to multiple and repeated injections, is therefore of utmost importance in the treatment of this disease. Indeed, samples of FvW with insufficient purity, obtained by fractionation of human plasma, contain various contaminants (residual proteins) capable to induce undesirable immunological reactions. Moreover, the administration of von Willebrand factor associated with Factor VIII may cause the risk of thrombosis or hypercoagulability in the treated patient (Makris et al, Thromb. Haemost. 88, 2002, pp. 377-378, Manucci P. M., Thromb. Haemost. 88, 2002, pp. 378-379).

Various processes for the preparation of FvW concentrates are typically associating steps of precipitation of a plasma fraction intended to remove the major part of undesirable proteins (fibrinogen, fibronectin, etc.), and/or chromatographies (ion exchange, affinity, immunoaffinity, size exclusion, etc.) aiming at obtaining very high purity concentrates, exhibiting a high specific activity and permitting to preserve the integrity of multimetric forms, especially those of high molecular weight, which are of utmost biological importance in the healing processes.

By way of example, reference can be made to the patent EP 0 359 593 which discloses the separation of proteins of a cryoprecipitated fraction of plasma implementing several steps of anion exchange chromatography leading to the purification of FvW.

The patent EP 0 503 991 discloses a process for preparing an industrial-scale FvW concentrate including a pre-purification step of a cryoprecipitated fraction of plasma and three successive chromatography steps, the third one being an affinity chromatography on a column of gelatine immobilized on agarose. The thus obtained FvW concentrate exhibits a specific activity higher than 100 UI RCo/mg expressed in ristocetine cofactor activity units per mg of proteins and a content of high molecular weight multimers comparable with that in the starting plasma.

The Patent Application EP 0 934 748 describes a process for the preparation of FvW including the combination of anion exchange and cation exchange chromatographies. The obtained FvW fractions exhibit a specific activity higher than 100 IU FvW:Ag/mg expressed in FvW antigen units per mg of protein, but still contain notable proportions of Factor VIII.

The patent U.S. Pat. No. 6,579,723 describes a process for preparing a highly purified FvW by immunoaffinity chromatography wherein the immunoadsorbents are anti-FvW antibodies. An additional step of purification by affinity chromatography on heparin can also be provided. However, the drawback of the purification by immunoaffinity is the possible presence of residual antibodies that can lead to immunological reactions.

The patent EP 0 383 234 teaches the preparation of a pasteurised FvW concentrate by means of an anion exchange chromatography, involving acidic solutions (pH of 5.5 to 6.5) containing carbohydrates, in order to fix the Factor VIII on the anion exchanger. The joint recovery of not-retained FvW, fibronectin and fibrinogen by washing of the support requires further precipitation steps in order to isolate a purified FvW concentrate.

The drawback of the above described processes lies in that they require several successive steps, especially chromatographic steps, causing problems related to the yield and to the clumsiness of the industrial-scale implementation. The processes can use, depending on the case, chromatographic supports with ligands of animal origin, such as based on gelatine, on heparin or on collagen, capable of acting as vectors of pathogenic prions responsible of spongiform encephalopathy, or of other viruses of the considered animal species. These difficulties are even amplified owing to the necessity to include in the process a virus inactivation treatment and, if need be, additional steps for the removal of virucide agents. Besides, the FvW concentrates obtained by these processes are not free from Factor VIII that represents the drawback of risk of thrombosis for the patients. Furthermore, the cleaning or washing of the affinity supports and their sanitation as well are difficult because of the fragility of the ligand, that prevents the use of cleaning solutions with a strong disinfectant character (sodium hypochlorite, soda, potassium hydroxide, etc.). Finally, the affinity supports have rather short lifetimes and their frequent replacement represents relatively high expenses, that are a burden to the cost price of the treated product.

Considering the continuously growing needs of high purity FvW fractions, the Applicant attempted to develop a new process for the preparation of FvW, which can be implemented by very simple means, giving a high yield, without the need to use chromatographic supports with ligands of animal origin and leading to a standardized high purity FvW concentrate endowed with a high specific activity and free from Factor VIII.

SUMMARY OF THE INVENTION

To that effect, the invention relates to a process for the preparation of a very high purity von Willebrand factor concentrate from a biological fraction containing von Willebrand factor, characterized in that it includes a separation by anion exchange chromatography using a vinyl polymer support of weak base type, the said separation including the steps of
a) loading the chromatographic support with the fraction containing von Willebrand factor, previously equilibrated with a suitable buffer, with a predetermined flowrate, that allows the retention of the von Willebrand factor;
b) washing of the support with an acidic buffer with a flowrate higher than that of the step a) until the proteins and the not-retained contaminants are removed;
c) flushing and equilibrating of the chromatographic support with the buffer and using the flowrate of the step a); and
d) elution of the von Willebrand factor by increasing the ionic strength of the buffer of the step c).

Thus, the Applicant found that it was possible, owing to a very simple process, to obtain a FvW concentrate with an increased quality, high specific activity and substantially free from Factor VIII. More precisely, the Applicant was able to demonstrate that the judicious choice of the chromatographic anion exchange support of vinyl polymer type and the particular physico-chemical conditions of the washing of this support (acidic pH, increased flowrate) allowed the separation, in a unique step, of the FvW retained on this support, from the rest of the proteins, especially the Factor VIII, and the other contaminants present in the biological fraction containing the FvW.

DETAILED DESCRIPTION OF THE PREFERRED EMBODIMENTS

Advantageously, the chromatographic separation is carried out on a synthetic support, a resin or gel, which matrix is of vinyl polymer type, representing more preferably a copolymer of oligoethylene glycol, of glycidyl-methacrylate and of pentaerythritol methacrylate, on which are grafted anion exchange groups of weak base type, such as DEAE. Such vinyl polymer matrices are known as Fractogel®-TSK and, in the scope of the invention, the anion exchangers supports are particularly the DEAE-Fractogel®-TSK 650 available with two particles sizes M (medium grade) and S (superfine grade), and number of studies are dedicated to their use. The chromatographic support is usually present as chromatographic columns with dimensions suited to the desired applications (analytical or preparative column).

The Applicant took therefore advantage of the rigidity characteristics and of the large size of pores of this support in order to carry out the process, which permitted to prevent the accumulation of some proteins tending to precipitate under acidic conditions during the chromatography, such as the fibronectin and the fibrinogen, thus avoiding the clogging of the support, without having to add large amounts of sugar as described in the patent EP 0 383 234. To this effect, the non-accumulation of these proteins has been made possible especially by an increasing of the flowrate during the washing phase, also owing to their important relaxation time to reach the pH conditions of the acidic buffer, with regard to their molecular weight (>300 kDa), and owing to their low content in the starting samples, that is limiting the probability of their meeting that could succeed in forming polymers or aggregates in situ.

In the scope of the invention, the biological fraction containing the von Willebrand factor is either the human plasma or a cryoprecipitated fraction of human plasma, or a supernatant of cryoprecipitated plasma still containing FvW, or obtained by way of classical fractionation processes (Cohn et al, J. Am. Chem. Soc., 68, 459, 1946, and Kistler et al, Vox Sang., 7, 1962, 414-424), optionally subjected to a pre-purification treatment, such as adsorption on aluminium hydroxide, wherein the FvW is complexed with the Factor VIII, or else yet a fraction enriched by a recombinant complex Factor VIII/FvW isolated from the supernatant of cell cultures in accordance to known techniques or, finally, from a Factor VIII/FvW complex obtained in the milk of transgenic mammals, as described in the patent U.S. Pat. No. 6,518,482. With particular preference, the starting fraction is a fraction of FvW obtained by a preliminary purification step of a cryoprecipitated fraction of plasma by chromatography using an anion exchanger of DEAE-Fractogel®-TSK 650 type, such as described in the patents EP 0 359 593 and EP 0 503 991. This preliminary step offers the advantage of recovery of the major part of the proteins of interest, such as the Factor VIII, the fibrinogen and the fibronectin.

The equilibration buffer (step a) or c)) contains sodium chloride in a concentration preferably of 0.11M, and may further comprise trisodium citrate, calcium chloride, glycine and lysine, at a pH of 6.9-7.1, the concentration of each component being preferably of 0.01M, 0.001M, 0.12M, and 0.016M, respectively. Use can also be made of any other buffer based on sodium chloride, comprising other biologically compatible compounds provided that they do not cause an irreversible denaturation of the FvW.

After the fraction containing FvW was applied onto the chromatographic support, a washing is carried out by percolation of the acidic buffer (step b)). The acidic buffer is advantageously composed of an alcaline or earth-alcaline salt of the acetic acid, citric acid or phosphoric acid, with a concentration in the range of between 10 and 30 mM, with a pH of 3.9-5.2, and is preferably a sodium acetate buffer 20 mM, of a pH 4.35 approximately. This washing step enables the proteins such as fibronectin, fibrinogen, Factor VIII, etc., and the not-retained or weakly retained contaminants on the support, present in the starting biological fraction, to pass into the filtrate. This step is carried out by increasing the flowrate used in the step a). In this way, the accumulation of the proteins and of the contaminants tending to precipitate can be avoided without the need of sugars addition that would be necessary to remove afterwards. The flowrate of the present washing step is judiciously chosen in order to obtain the sought-after effect making sure that the physico-chemical properties of the chromatographic support are not altered by the excessive values of the flowrate. Preferably, the value of the washing flowrate corresponds to a higher value than that of the equilibrating step a) by a factor of about 1.5 to 2. The duration of the washing is determined by measurement of the optical density (OD) of the filtrate at a wavelength of 280 nm. Indeed, a value of the OD corresponding to the baseline value is a good indication that the above-mentioned compounds are effectively removed from the support and left the chromatographic column.

After returning to the baseline, the flowrate is reduced to the value of that of the step a) and the elution of the FvW (step d)) is carried out by using a buffer of the step a), the ionic strength of which is increased. This increase of the ionic strength is advantageously carried out by addition of sodium chloride, the final concentration of which is adjusted to 0.15-0.17M. The use according to the invention of the chromatographic support with a vinyl polymer matrix of the invention, of a slightly hydrophobic nature, allows the separation of the FvW from impurities and/or accompanying proteins, such as fibronectine. Surprisingly, the FvW obtained by the process is free from Factor VIII.

The process of the present invention can be adapted to volumes of plasma of about 4000 liters.

The process can comprise at least one step of a virus inactivation treatment of the fraction containing the FvW to be purified. Thus, the fraction could be subjected to a classical virus inactivation treatment by solvent-detergent in the presence of inactivating agents, such as Tween®-TNBP, before the chromatographic step, the last one enabling to efficiently eliminate the residual products of this decontamination step.

Particularly, the fraction of FvW, once harvested, could be subjected to various treatments intended to obtain a product of therapeutic quality. Thus, after the step d), the process may include one or more further steps consisting of a classical sterile filtration, then a virus elimination filtration, such as a nanofiltration on a filter of 35 nm. Then the fraction of FvW can be subjected to a diafiltration in order to incorporate suitable excipients that will allow to use a dry heat treatment of the FvW without the risk of denaturation, to a concentration by ultrafiltration, to a conditioning in vials and lyophilisation, after a previous addition of a further pharmaceutically acceptable stabilizer, such as albumin. Finally, the lyophilisates are subjected to an ultimate virus inactivation step by dry heat treatment of the lyophilisate in classical conditions, at 80° C. for 72 hours, in order to inactivate the non-enveloped viruses that would not have been inactivated and/or eliminated by means of at least one of the two preceding virus inactivation and/or elimination steps. The dry heated lyophilisates are then reconstituted with an aqueous medium suitable for clinical use, preferably in 10 ml of purified water for injection (PPI) that can be directly injected intravenously.

Thus, the implementation of the process, after the ultrafiltration step, leads to a highly purified FvW concentrate of therapeutic quality, exhibiting a specific activity (S.A.) of at least 90 IU RCo/mg of protein. Moreover, the ratio of R, representing the Factor VIII:C/FvW:RCo, is less than 0.06%. This result shows that the FvW concentrate is free from Factor VIII, or contains only insignificant amounts thereof.

The total degree of purification of the present process is higher than 10 000 when using a biological fraction of plasma.

The final product of FvW obtained, i.e. the lyophilisate of the heated FvW reconstituted with water PPI, exhibits a content of multimers, measured in reference to the Method 0275 of the European Pharmacopoeia, comparable with that of the plasma, which is of 70%. The residual contents of TNBP and Tween® are also in accordance with the values set by the European Pharmacopoeia.

The stability of the FvW concentrate (after ultrafiltration) was observed for a period of 24 hours at room temperature: no trace of proteolysis was detected. Moreover, the final lyophilised product of FvW remains stable during a storage time of about 2 years at 30° C. and for six months at 40° C. It exhibits a Factor VIII binding capacity similar to that of the FvW present in the native plasma.

The invention also relates to a von Willebrand factor concentrate for therapeutic use obtainable by the above-described process from a biological fraction containing von Willebrand factor, wherein the rate of Factor VIII:C/FvW:RCo is less than 0.06%.

The following examples illustrate the method of implementing the present invention without, however, limiting its scope.

EXAMPLE 1

1) Obtention of a FvW Containing Fraction

A cryoprecipitate of human plasma is used, suspended in an aqueous solution of sodium heparin (at 2 U/ml), with a pH of 7-7.1.

This suspension of cryoprecipitate is subjected to a prepurification on aluminium hydroxide in order to remove the main contaminants, such as described in the patent EP 359 593. The pre-purified supernatant is then recovered and subjected to a classical virus inactivation treatment by solvent-detergent, in the presence of Tween®-TNBP.

The solution of pre-purified cryoprecipitate is then injected onto a chromatographic column of DEAE-Fractogel®-TSK 650 (M) of 25 cm of length and 1 cm of diameter, previously equilibrated with a buffer containing trisodium citrate 0.01M, calcium chloride 0.001M, sodium chloride 0.11M, glycine 0.12M and lysine 0.016M, adjusted to a pH 7.01, the linear velocity of the mobile phase being set to 100 cm/hour. The FvW, the Factor VIII and the fibronectin are retained on the chromatographic support. The weakly retained or not-retained proteins on the support, mainly fibrinogen and IgG, are removed in the filtrate, and the Tween® and TNBP as well, by several subsequent washings with the same buffer.

When the OD, measured at 280 nm, has dropped back to the baseline value, the sodium chloride concentration of the buffer is increased to 0.15M. The FvW is eluted in these conditions. The thus obtained eluate is highly enriched by Fvw and fibronectin and still contains Tween® and TNBP, and residual Factor VIII as well.

2) Chromatographic Separation

The previously eluted fraction enriched by FvW, forming a batch of starting FvW fraction of the invention, is charged onto a chromatographic column of DEAE-Fractogel®-TSK 650 (M) of 25 cm of length and 1 cm of diameter, previously equilibrated with the same buffer as that of 1), with an osmolarity of 387 mosmolkg$^{-1}$, the linear velocity of which is set to 100 cm/hour. 140 ml of this fraction containing 12.9 IU of FvW/ml and 6.6 IU of Factor VIII/ml, that is to say a rate R of 51.1% (R=FVIII:C/FvW:RCo), are injected.

The column is then washed with a sodium acetate 20 mM acidic buffer, adjusted to a pH 4.35 and 80 mosmolkg$^{-1}$, with a linear velocity of 150 cm/hour. In these conditions, a very high rate of elimination of not only residues of the virus inactivation agents but also of the fibronectin and, above all, of the Factor VIII that was still complexed with FvW, is ensured without observing any precipitation of these proteins in the column. When the OD has dropped back to the baseline value, the linear velocity is brought back to 100 cm/hour, and the column is flushed and equilibrated with the same buffer as above, containing NaCl 0.11M.

The fraction containing the FvW is eluted by increasing the NaCl concentration of the equilibration buffer to 0.17M, adjusted to a pH of 6.95 and 492 mosmolkg$^{-1}$.

The eluted FvW fraction is subjected to classical treatments consisting of a sterile filtration on filters of 0.22 μm, a nanofiltration on filters of 35 nm, a diafiltration against a solution containing arginine, at least one hydrophobic amino acid and trisodium citrate, as described by the Applicant in the Patent Application FR 03 08403, and an ultrafiltration according to known techniques in such a manner that the FvW concentrate exhibits a specific activity (S.A.) of at least 90 IU RCo/mg of protein.

Albumin of 10 g/l is added to the thus obtained FvW concentrates, then the concentrates are lyophilised at −40° C, for 48 hours. The lyophilisation is followed by a heat treatment of virus inactivation by dry heat treatment of the lyophilisate at 80° C. for 72 hours.

In order to compare the performances of the process of the invention related to the quality of the FvW concentrate obtained in terms of specific activity, residual content of various proteinaceous contaminants, especially of Factor VIII, comparisons were carried out using the FvW concentrate obtained by using the process described in the Patent EP 0 503 991, designated as process A.

The implementing of the process according to this patent includes the following steps consisting of:

passing of a batch of FvW fraction resulting from the first chromatographic separation described in 1) onto a second chromatographic column 25 cm of length and 1 cm of diameter containing DEAE-Fractogel®-TSK 650 (M) carried out in the conditions as described 1) (same buffer, same linear velocity);

removal of the filtrate and flushing of the column with the equilibration buffer;

elution of the FvW by increasing the concentration of NaCl in the equilibration buffer to 0.17M;

subjecting the FvW eluate to an additional purification step on a column wherein the chromatographic support is of gelatine immobilized on agarose type equilibrated with the equilibration buffer, intended to remove the residual fibronectin.

The eluate of this ultimate chromatographic step is afterwards subjected to the same treatments consisting of a sterile filtration, a virus eliminating filtration, a diafiltration, an ultrafiltration, an addition of albumin, a lyophilisation and a dry heat treatment.

In the Table 1 are resumed the results of the yields of preparation of FvW fractions expressed in IU RCo/mg of protein at various stages of the process according to the invention and according to A, i.e. after all the chromatographies, ultrafiltration, and after lyophilisation, dry heat treatment (80° C., 72 hours), and reconstitution with 10 ml of purified water for injection (PPI). The lyophilisate of the starting FvW fraction is subjected to the same treatments by ultrafiltration and by dry heating, followed by a reconstitution with 10 ml of water PPI. The yields are expressed in rates of:

$$R1 = \frac{S.A. \text{ of the starting } FvW \text{ fraction}}{S.A. \text{ of the } FvW \text{ fraction after chromatographies}}$$

$$R2 = \frac{S.A. \text{ of the ultrafiltrated starting } FvW \text{ fraction}}{S.A. \text{ of the eluted and ultrafiltrated } FvW \text{ fraction}}$$

$$R3 = \frac{S.A. \text{ of the heated lyophilisate starting } FvW \text{ fraction}}{S.A. \text{ of the heated lyophilisate } FvW \text{ fraction}}$$

The S.A. (IU RCo/mg), measured on the FvW concentrate and the corresponding contents of residual fibronectin (TFR) are shown as well.

The shown values are the average values of six assays.

TABLE 1

| n = 6 | R1 (%) | R2 (%) | R3 (%) | As* | TFR μg/IUFvW:R Co |
|---|---|---|---|---|---|
| FvW fraction of the invention | 87 ± 5 | 97.9 ± 5.2 | 84.1 ± 6.1 | 98.7 ± 5.6 | <0.04 |
| FvW fraction in accordance to A | — | 89.4 ± 5.7 | 84.1 ± 11.6 | 98.3 ± 14.5 | <0.04 |

*S.A. measured on the FvW concentrate

Both processes are comparable and give in both cases FvW concentrates with a satisfactory yield and with high S.A.

The Table 2 shows the results of different assays in order to assess the rate of residual proteinaceous and chemical contaminants in a dry heated FvW lyophilisate and reconstituted with 10 ml of water PPI, obtained according to the invention (Product I) and according to A (Product II). The given values represent average values of six assays.

TABLE 2

|  | Product I | Product II |
|---|---|---|
| Activity FVIII:C (IU/ml) | 0.035 ± 0.025 | 1.8 to 9.2 |
| R | 0.035 ± 0.025 | 1.84 to 8.85 |
| Protein content (g/l) | 9–10 | 11.25 ± 0.25 |
| Tween ® content (mg/l) | <20 | <20 |
| TNBP content (mg/l) | <0.1 | <0.1 |

There is a considerable difference between the concentrate obtained according to the process A and that obtained according to the invention with regard to the rate R (FVIII:C/FvW:RCo). Indeed, the concentrate obtained according to the invention is nearly free of measurable FVIII:C.

The Table 3 shows the results of yields, of specific activities and of contents of residual fibronectin, obtained from the same batch of starting FvW fraction, divided in two equal fractions of FvW, of which one is subjected to the process of the invention and the other fraction is subjected to the process according to A. The yields are measured at different stages of the processes according to the conditions described for results of the Table 1. The given values are average values of six assays.

TABLE 3

| n = 6 | R1 (%) | R2 (%) | R3 (%) | As* | TFR µg/IUFvW:R Co |
|---|---|---|---|---|---|
| FvW fraction of the invention | 89 ± 10 | 88 ± 12 | 86.3 ± 9.2 | 98.7 ± 5.6 | <0.04 |
| FvW fraction according to A | 87 ± 10 | 76.3 ± 7.5 | 70 ± 8 | 98.3 ± 14.5 | <0.04 |

*S.A. obtained on the FvW concentrate

The results in the Table 3 show clearly that the quality of the final product of FvW obtained according to the process of the invention is at least equal to that obtained by the process according to A, and that the yields are comparable.

The Table 4 shows the content of various proteins present in a lyophilised and in a dry heated FvW fraction and reconstituted with 10 ml of water PPI, obtained according to the process of the invention (Product III) and according to the process A (Product IV). The given values are the average values of three assays.

TABLE 4

| n = 3 | Product III | Product IV |
|---|---|---|
| FVW (µg/ml) | 1022 ± 57 | 1015 ± 72 |
| FVIII (µg/ml) | 0.14 ± 0.08 | 1.82 ± 0.53 |
| Fibrinogen (µg/ml) | 8.2 ± 5.2 | 3.5 ± 1.2 |
| Fibronectin (µg/IU FvW:RCO) | >0.04 | >0.04 |
| Immunoglobulin G (µg/ml) | 1.93 ± 0.71 | 4.23 ± 0.95 |
| Immunoglobulin A (µg/ml) | 1.4 | 2.23 ± 0.46 |
| Immunoglobulin M (µg/ml) | <8.5 | 28.8 ± 8.9 |
| Inter-α-trypsin inhibitor (µg/ml) | 14.83 ± 5.25 | 1.93 ± 0.83 |
| Plasminogen (µg/ml) | 0.006 | 0.0106 ± 0.0022 |
| Protein C (µg/ml) | <2.5 | <2.5 |

The results in the Table 4 show that the FvW fraction of the invention exhibits a markedly lower content of FVIII and of immunoglobulins M than that achieved by using the process A. On the other hand, it contains a higher amount of inter-a-trypsin inhibitor (ITI), however, it is not detrimental to the therapeutic properties of the FvW concentrate, unlike to the parameter of the measurable content of FVIII.

EXAMPLE 2

Use is made of various fractions containing FvW, obtained from a cryoprecipitate having been subjected to the treatment described in the Example 1, 1). These FvW fractions are adjusted in such a manner that they contain a variable amount of the initial rate R (FVIII:C/FvW:RCo) spreading of about 30% to about 120%.

These fractions are afterwards subjected to a chromatographic separation according to the invention and according to the process A and to various treatments resulting in dry heated lyophilisates reconstituted with water PPI, according to the conditions described in the Example 1, 2).

The results of the yields are shown in Table 5.

TABLE 5

| R initial | 32.6% | 51% | 64.6% | 120.8% |
|---|---|---|---|---|
| Yield of FvW according to A (%) | 92.9 | 47.4 | 46.8 | 97.4 |
| Yield of FvW according to the invention (%) | 93.1 | 53.4 | 95.7 | 104 |
| R according to A (%) | 8.8 | 22.8 | 10.6 | 21.3 |
| R according to the invention (%) | 0 | 0.05 | 0 | 0 |

Thus, the implementing of the process of the invention leads to a nearly total elimination of FVIII, while giving an increased production yield.

The invention claimed is:

1. A process for preparing a von Willebrand factor concentrate from a biological fraction containing von Willebrand factor, said process comprising separating said von Willebrand factor by anion exchange chromatography using a vinyl polymer support of a weak base type, said separation comprising the steps of:
   a) loading the anion exchange chromatographic support equilibrated with a suitable buffer with the fraction containing the von Willebrand factor, wherein said loading is performed at a flowrate at which the anion exchange chromatographic support retains the von Wiliebrand factor;
   b) washing the loaded anion exchange chromatographic support with an acidic buffer with a flowrate 1.5-2 times higher than that of step a) until the weakly retained contaminants are removed, wherein the pH of said acidic buffer is of pH 3.5- 5.2;
   c) flushing and equilibrating the chromatographic support with the equilibrating buffer and the flowrate of the step a); and
   d) eluting the von Willebrand factor concentrate from the anion exchange chromatographic support by increasing the ionic strength of the buffer of the step c).

2. The process of claim 1, wherein the chromatographic separation is carried out on a support of vinyl polymer type grafted with anion exchange groups of diethylaminoethyl.

3. The process of claim 1, wherein the chromatographic separation is carried out on a support of vinyl polymer type grafted with anion exchange groups of diethylaminoethyl representing the diethylaminoethyl-Fractogel®-TSK 650.

4. The process of claim 1, wherein the buffer of step a) or c) comprises sodium chloride.

5. The process of claim 1, wherein the buffer of steps a) and c) comprises 0.11 M sodium chloride.

6. The process of claim 4, wherein said buffer further comprises trisodium citrate, calcium chloride, glycine and lysine, at a pH of 6.9-7.1.

7. The process of claim 1, wherein said buffer of the step a) or c) is composed of sodium chloride, further comprising trisodium citrate, calcium chloride, glycine and lysine, at a pH of 6.9-7.1, the concentrations of which are 0.01M, 0.001M, 0.12M and 0.016M respectively.

8. The process of claim 1, wherein said acidic buffer comprises an alkaline or earth-alkaline salt of said acetic acid, citric acid or phosphoric acid, with a concentration between 10 and 30 mM and with a pH 3.5-5.2.

9. The process of claim 8, wherein said acidic buffer is a sodium acetate buffer 20 mM with a pH of 4.35.

10. The process of claim 1, wherein in step d), the ionic strength of the buffer of step c) is increased by adding sodium chloride the final concentration of which is adjusted to 0.15-0.17M.

11. The process of claim 1, further comprising a step of virus Inactivation by treating said biological fraction with solvent-detergent.

12. The process of claim 1, further comprising, after elution step d), one or more further steps consisting of:

sterile filtration;
virus elimination filtration;
diafiltration;
concentrating ultrafiltration;
addition of a pharmaceutically acceptable stabilizer;
lyophilisation;
virus inactivation by a dry heat; and
reconstitution of the heated lyophilisate with an aqueous medium suitable for clinical use.

13. A von Willebrand factor concentrate prepared by the process of claim 1, having a rate of Factor VIII:C/FvW:RCo of less than 0.06%.

* * * * *